US00PP28004P3

(12) United States Plant Patent
O'Connell

(10) Patent No.: US PP28,004 P3
(45) Date of Patent: May 9, 2017

(54) ***ECHEVERIA* PLANT NAMED 'COLORSHIFT'**

(50) Latin Name: ***Echeveria* hybrid**
Varietal Denomination: COLORSHIFT

(71) Applicant: Renee O'Connell, Escondido, CA (US)

(72) Inventor: Renee O'Connell, Escondido, CA (US)

(73) Assignee: Altman Specialty Plants, Inc, Vista, CA (US)

( * ) Notice: Subject to any disclaimer, the term of this patent is extended or adjusted under 35 U.S.C. 154(b) by 77 days.

(21) Appl. No.: 14/544,920

(22) Filed: Mar. 6, 2015

(65) Prior Publication Data

US 2016/0270279 P1 Sep. 15, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Cassandra Bright

(57) ABSTRACT

A new and distinct *Echeveria* cultivar named 'Colorshift' is disclosed, characterized by unique "colorshifts" of the rosette, dependent upon ambient conditions caused by seasonal changes, not observed in comparable *Echeverias*. The new variety exhibits variability of rosette color that can include violet, silvered mauve, silvered aqua and their intermediate colors. The cultivar 'Colorshift' also exhibits light margin colors, strongly accenting the multi-hued violet rosette. In addition, the new cultivar 'Colorshift' produces a display of bright, vermillion flowers, accenting the violet rosette, a contrast not exhibited by comparable *Echeveria* varieties. The new variety exhibits a robust growth habit, enabling faster production, than most comparable *Echeveria* varieties.

6 Drawing Sheets

Latin name of the genus and species: *Echeveria* hybrid.
Variety denomination: 'COLORSHIFT'.

BACKGROUND OF THE INVENTION

The new *Echeveria* cultivar is the product of a planned breeding program. The new variety originated from a cross pollination of the proprietary, unpatented, seed parent, *Echeveria* 'L1-Y13' with the pollen parent an unpatented, proprietary variety of *Echeveria* referred to as 'A5-S17.' The cross pollination was made during March of 2010 in Vista, Calif., at a commercial greenhouse. The new cultivar 'Colorshift' was discovered by the inventor, Renee O'Connell, in February of 2011, in Vista, Calif. at the same commercial greenhouse.

The seed parent is the, unpatented, proprietary variety referred to as *Echeveria* 'L1-Y13'. The pollen parent is the unpatented, propriety variety referred to as *Echeveria* 'A5-S17'. The new variety was discovered in February of 2011 by the inventor in a group of seedlings resulting from the 2010 crossing, in a commercial greenhouse in Vista, Calif.

Asexual reproduction of the new cultivar 'Colorshift' was first performed in Vista, Calif., at a commercial greenhouse, by vegetative cuttings in April of 2011. 'Colorshift' has since produced multiple generations and has shown that the unique features of this cultivar are stable and reproduced true to type.

SUMMARY OF THE INVENTION

The cultivar 'COLORSHIFT' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'COLORSHIFT' These characteristics in combination distinguish 'COLORSHIFT' as a new and distinct *Echeveria* cultivar:

1. Exhibits color change of the rosette, in reaction to changes in ambient conditions, such as changes in light intensity, temperature, and day length, not found in comparable *Echeveria*.
2. Produces hyaline margins, contrasting dramatically with the variable rosette colors, a characteristic not found in comparable *Echeveria*.
3. Floriferous plants, producing inflorescences of large, bright vermillion flowers, not observed with comparable *Echeveria*.
4. Much more easily and rapidly propagated due to robust growth.

Plants of the new cultivar 'COLORSHIFT' are similar to plants of the seed parent, *Echeveria* 'L1-Y13' in most horticultural characteristics, however, plants of the new cultivar 'COLORSHIFT' differ in the following;

1. Exhibit a unique color change as a reaction to changes in ambient environment, not exhibited by the seed parent.
2. More robust, faster growing.
3. Manifest a hyaline margin that contrasts dramatically with the rosette, whereas the seed parent does not exhibit this quality.
4. The flowers of the new cultivar are much larger than those of the seed parent and have a "glowing" quality that is not exemplified by the seed parent.
5. Greater resistance to diseases and pests.

Plants of the new cultivar 'COLORSHIFT' are similar to plants of the pollen parent, *Echeveria* 'A5-S17' in most horticultural characteristics, however, plants of the new cultivar 'COLORSHIFT' differ in the following;

1. Exhibits more undulating, brighter colored leaf margins than the pollen parent.
2. Exhibits a unique color change as a reaction to changes in ambient environment, not exhibited by the pollen parent.
3. Flowers of the new cultivar are more vivid in color than those of the pollen parent.
4. Greater resistance to diseases and pests.

COMMERCIAL COMPARISON

Plants of the new cultivar 'COLORSHIFT' are comparable to the unpatented, commercial variety *Echeveria* 'Afterglow'. The two *Echeveria* varieties are similar in most horticultural characteristics; however, the new variety 'COLORSHIFT' differs in the following:

1. Forms a more concentric rosette than *Echeveria* 'Afterglow', producing a more uniform, aesthetic rosette plant form.
2. Exhibits color change of the rosette, not observed in *Echeveria* 'Afterglow'.
3. Manifests hyaline margins in contrast to rosettes, a quality not observed with *Echeveria* 'Afterglow'.

Plants of the new cultivar 'COLORSHIFT' can also be comparable to the unpatented commercial variety *Echeveria* 'Perle von Nurnberg'. The two *Echeveria* varieties are similar in most horticultural characteristics; however, the new variety 'COLORSHIFT' differs in the following:

1. Exhibits much more concentric rosettes.
2. Exhibits color change of the rosette, not observed in *Echeveria* 'Perle von Nurnberg'.
3. Much more resistant to the pathogen *Rhizoctonia,*
4. Produces more vividly colored and larger flowers.

BRIEF DESCRIPTION OF THE PHOTOGRAPHS

The accompanying photographs in FIG. 1 through FIG. 6 illustrate in full color typical plants of 'COLORSHIFT' grown in a greenhouse in Vista, Calif. These photographs exhibit some of the variability of the cultivar due to ambient changes in environment. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Echeveria* plant. All photographs provided by the breeder.

Figure 1:
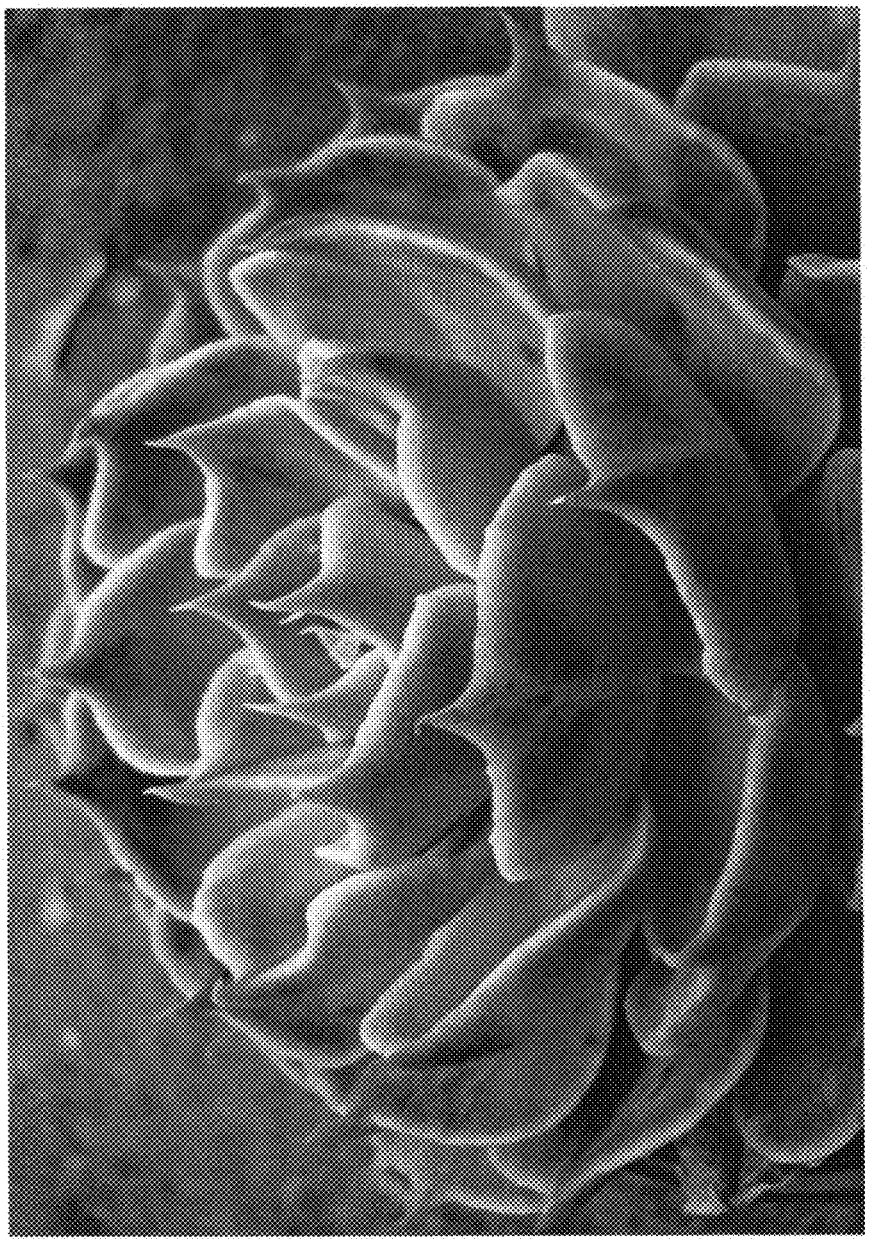
FIG. 1 illustrates a side view of a plant grown under high light conditions and short days showing both the under and upper sides of the foliage.
Figure 2:
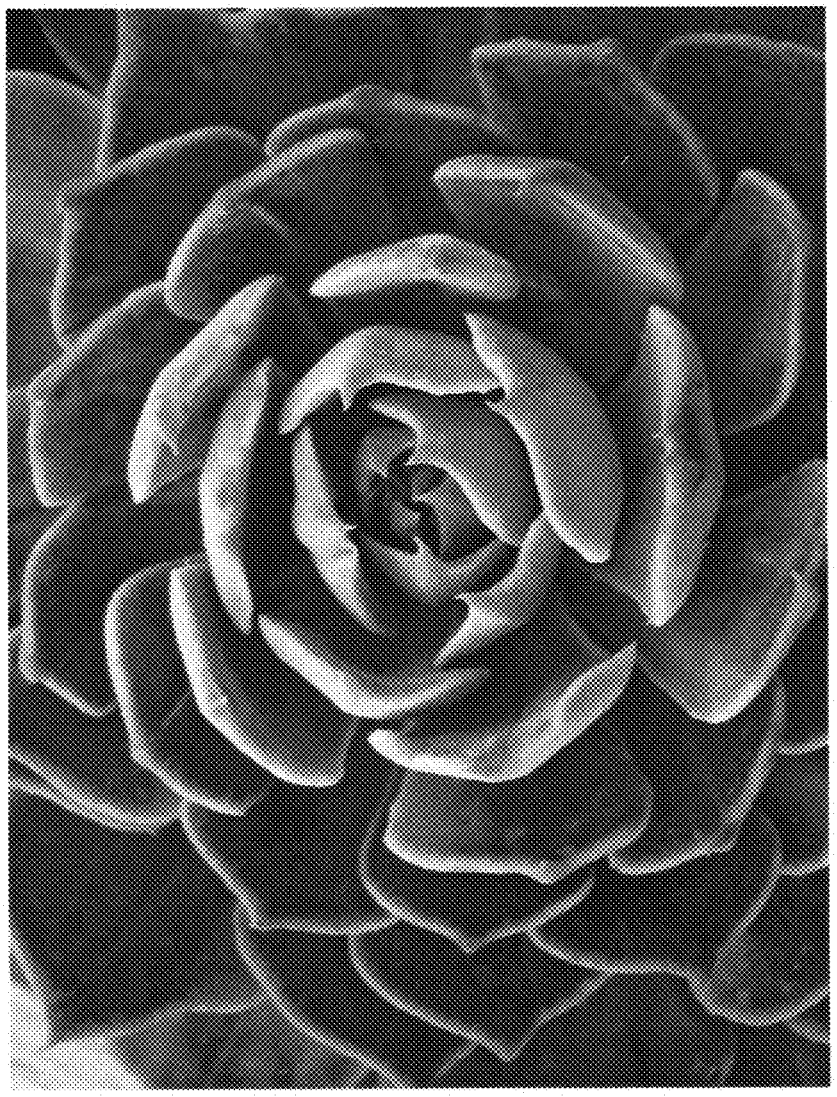
FIG. 2 illustrates a top view in close up the interior foliage whorl of a plant grown under lower light conditions and long days.
Figure 3:
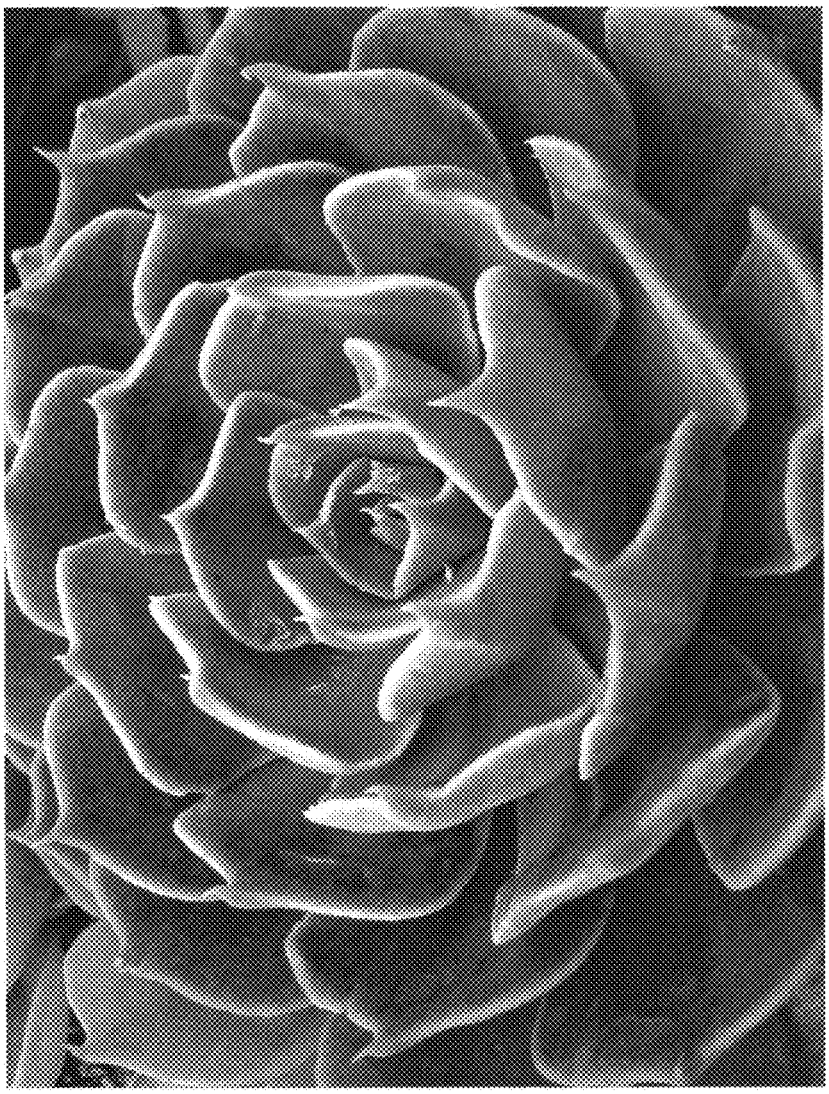
FIG. 3 illustrates a top view in close up the interior foliage whorl of a plant grown under high light conditions and long days.
Figure 4:
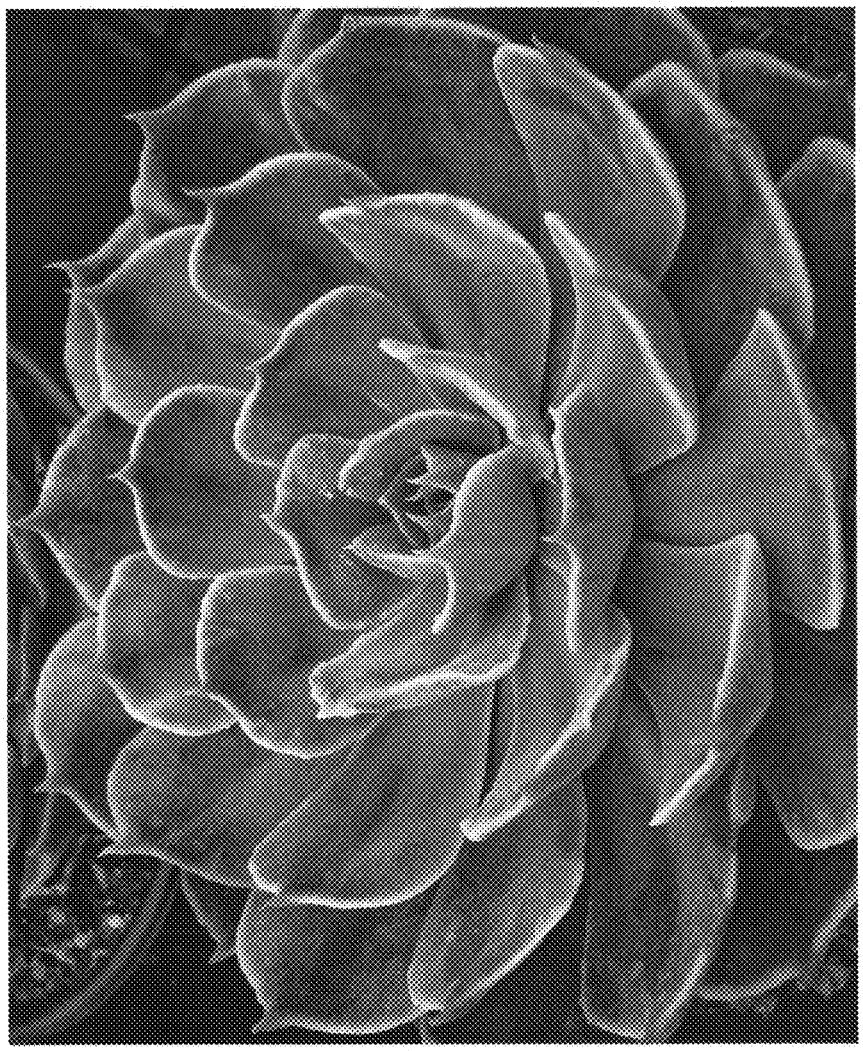
FIG. 4 illustrates a top view of a plant grown under lower light conditions and long days.
Figure 5:
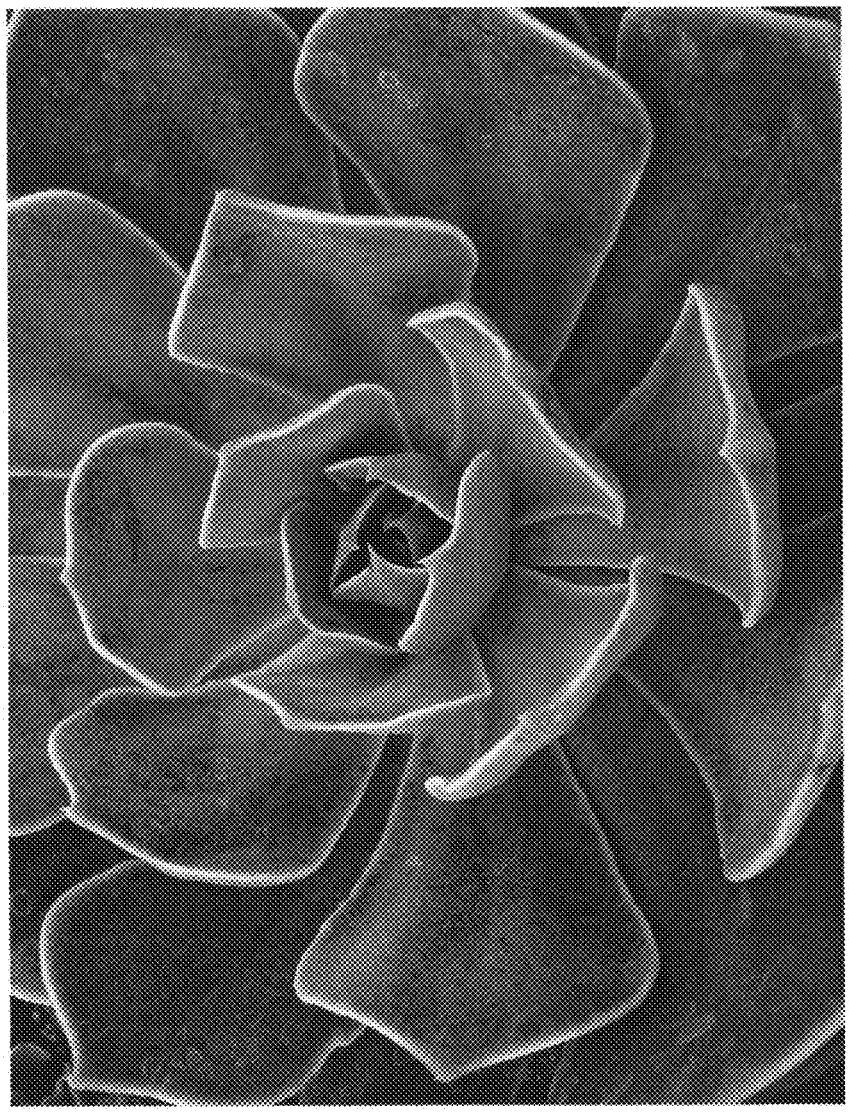
FIG. 5 illustrates a plant of grown under very lower light conditions and short days.
Figure 6:
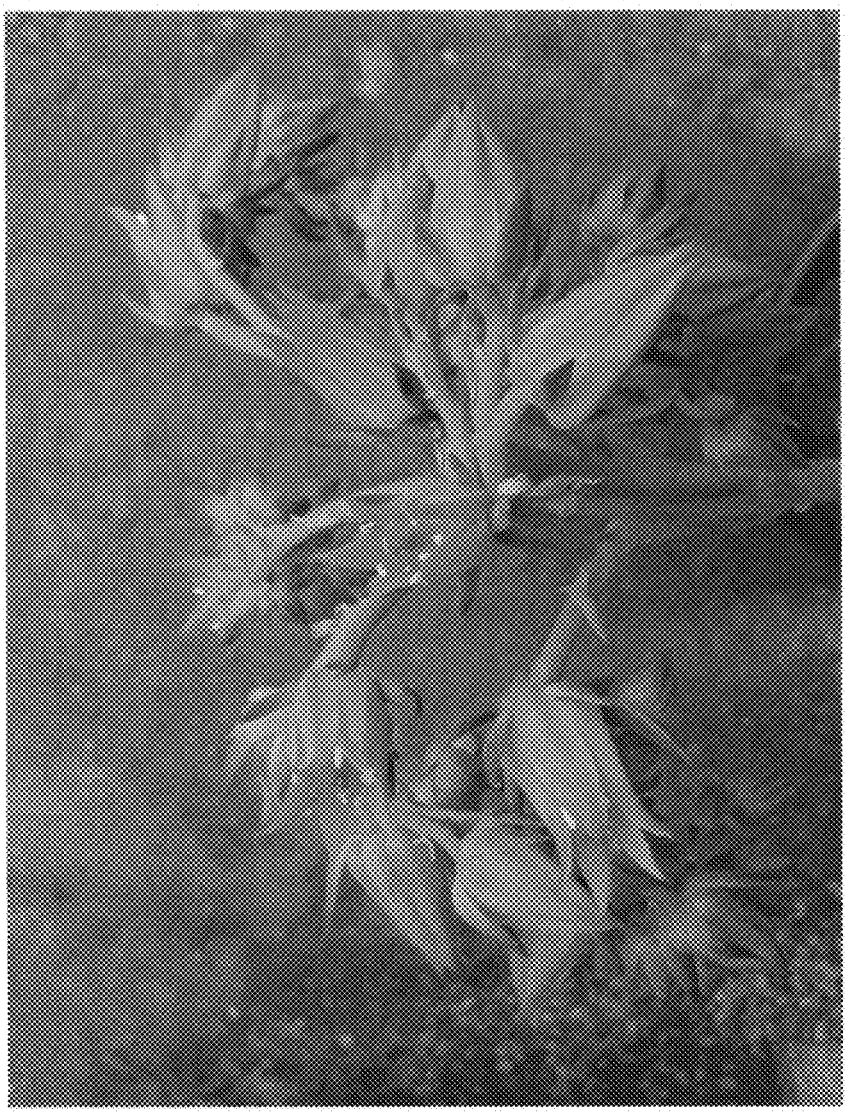

FIG. 6. Illustrates a close up of an inflorescence of the new variety.

DETAILED BOTANICAL DESCRIPTION

In the following description, color references are made to the Pantone Process Color System Guide, Pantone CYMK, 2014, except where general terms of ordinary dictionary significance are used. The following observations and measurements describe 'Colorshift' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'COLORSHIFT'.

PROPAGATION

Type of propagation typically used: Terminal vegetative divisions.

Time to initiate roots: About 17 days at approximately 21° C.

Root description: Fibrous.

PLANT

Age of plant described: Approximately 4 months.

Container size of the plant described: 14 cm.

Growth habit: Densely rosulate, sessile.

Height: Approximately 7 cm to top of highest leaf. Approximately 38 cm to top of highest inflorescence.

Plant spread: Approximately 16 cm.

Growth rate: Moderately fast.

Branching characteristics: Occasionally, when larger.

FOLIAGE

Leaf:

*Arrangement.*—Rosulate.

*Average length.*—Approximately 8.5 cm.

*Widest width.*—Approximately 3.5 cm.

*Width at base.*—1 cm.

*Shape of blade.*—Oblanceolate.

*Apex.*—Mucronate.

*Base.*—Cuneate.

*Margin.*—Entire.

*Texture of top surface.*—Glabrous, somewhat glaucous.

*Texture of bottom surface.*—Glabrous, glaucous.

*Quantity of leaves per plant.*—Approximately 64.

Color:

*Young foliage upper side, middle of leaf.*—Near P 108-9U Pantone.

*Young foliage, upper side, if glaucous covering is removed.*—Near P 178-12 U Pantone.

*Young foliage upper side, apex.*—Near P 55-9 U Pantone.

*Young foliage, upper side, base.*—Near P 30-1 U Pantone.

*Young foliage, upper side, margin.*—Near P 178-2 U Pantone.

*Young foliage, upper side, margin near base.*—Near P 30-1 U Pantone.

*Young foliage, under side*.—Near P 108-7 U Pantone.
*Young foliage underside, if glaucous covering is removed*.—Near P 178-10U Pantone.
*Young foliage under side, apex*.—Near P 55-1 Pantone.
*Young foliage, under side, base*.—Near P 30-1 U Pantone.
*Mature foliage upper side*.—Near P 177-6 U Pantone.
*Mature foliage upper side, apex*.—Near P 62-4 U Pantone.
*Mature foliage, upper side, base*.—Near P 6-9 U Pantone.
*Mature foliage upper side, margin*.—Near P 163-1 U Pantone.
*Mature foliage, upper side, margin, near apex*.—Near P 57-3 U Pantone.
*Mature foliage, upper side, margin, near base*.—Near P 7-1 U Pantone.
*Mature foliage, under side*.—Near P 109-1 U Pantone.
*Mature foliage, under side, if glaucous covering is removed*.—Near P 178-6 U Pantone.
*Mature foliage, under side, apex*.—Near P 79-10 U Pantone.
*Mature foliage, under side, near base*.—Near P 48-1 U Pantone.
*Mature foliage, under side, margin*.—Near P 159-2 U Pantone.
*Venation*.—There is no visual appearance of venation.

FLOWER

Natural flowering season: Spring, Autumn.
Inflorescence type and habit: Erect cyme with 3 bifurcate cincinni.
Rate of flower opening: 1 flower opens every 2-3 days, depending upon ambient conditions.
Flower longevity on plant: 3-4 days, depending upon ambient conditions.
Quantity of flowers: 63.

*Total inflorescence size*.—Height: Approximately 38 cm. Width: Approximately 14 cm.

*Corolla*.—Arrangement: Actinomorphic. Size: Length: Approximately 1.9 cm. Width: Approximately 1.1 cm at widest point. Lobe Length: Approximately 1.8 cm. Lobe width: Approximately 4.5 mm. Margin: Entire. Shape: Pentagonally campanulate, tubular. Apex: Acute. Texture: Glabrous. Color: Outer corolla: Near P 48-8 U Pantone. Outer corolla, apex: Near P 52-7 U Pantone. Inner corolla, near base: P 34-3 U Pantone. Inner corolla, apex: Near P 48-7 U Pantone. Corolla margin: Near P 20-5 U Pantone. Petal Color: When opening: Petal color, outer surface: Near P 52-6 U Pantone. Petal color, inner surface: P 48-7 U Pantone. Petal Color, Fully opened: Outer surface, near base: Near P 59-6 U Pantone. Outer surface, apex: Near P 48-7 U Pantone. Inner surface, apex: Near P 48-8 U Pantone. Color Changes when Aging: Near P 62-7 U Pantone. Bud: (near opening): Shape: Shortly conical. Length: Approximately 1.3 cm. Diameter: Approximately 0.56 cm. Color, Bud close to anthesis: Near P 55-15 U Pantone. In longitudinal bands; intermixed with longitudinal bands of P 7-11 U Pantone. A blush of color P 67-7 Pantone was observed near apex of bud. Bud: (further down stem; not close to opening): Length: Approximately 1 cm. Diameter: 0.5 cm. Bud: (further down stem: not close to opening): Color: Near P 48-3 U Pantone glaucous color over P 168-3 U Pantone. Sepals: Color, Back of sepal: Near P 79-11 U Pantone. Color, Front of sepal: Near P 79-12 U Pantone. Pedicels: Length: Approximately 1 cm. Width: Approximately 0.15 cm. Aspect: Spreading at 45°. Color: Near P 64-11 U Pantone.

*Fragrance*.—None detected.

REPRODUCTIVE ORGANS

Stamens: (Androecium).
*Number*.—Average 10.
*Filament length*.—Approximately 0.8 cm.
*Filament color*.—Near P 62-7 U Pantone.
*Anther length*.—0.25 cm.
*Anther color*.—Near P 7-6 U Pantone.
*Anther shape*.—Elliptic.
*Pollen color*.—Near P 7-5 U Pantone.
Pistil: (Gymnoecium).
*Number*.—Average 5.
*Length*.—Approximately 1.3 cm.
*Style color*.—Near P 10-9 U Pantone.
*Stigma*.—Shape: Round. Color: Near P 159-6 U Pantone. Ovary Color: Near P 11-5 U Pantone.

OTHER CHARACTERISTICS

Fruits and seeds: No outstanding differences noted from typical fruits and seeds.
Temperature tolerance: Tolerates temperatures from approximately −2 C to 32 C.
Disease/pest resistance: Increased resistance to normal diseases and pests of *Echeveria* has been observed.
Drought tolerance: Tolerates at least 3 weeks of high temperatures without supplemental water, showing no serious damage to plant.

What is claimed is:

1. A new and distinct cultivar of *Echeveria* plant named 'COLORSHIFT' as herein illustrated and described.

* * * * *